(12) United States Patent
Blecher et al.

(10) Patent No.: US 12,023,191 B2
(45) Date of Patent: Jul. 2, 2024

(54) APPARATUS FOR REAL-TIME VISUALIZING A MOVEMENT OF A LOWER JAW VERSUS AN UPPER JAW IN A CRANIOMAXILLOFACIAL AREA OF A PATIENT IN DENTAL DIAGNOSTICS

(71) Applicants: DENTSPLY SIRONA Inc., York, PA (US); SIRONA DENTAL SYSTEMS GMBH, Bensheim (DE)

(72) Inventors: Wolf Blecher, Hemsbach (DE); Franziska Riversa, Modautal (DE); Ulrich Schulze-Ganzlin, Lorsch (DE); Kai Lindenberg, Wersau (DE); Christian Beckhaus, Darmstadt (DE)

(73) Assignee: DENTSPLY SIRONA INC., York, PA (US)

( * ) Notice: Subject to any disclaimer, the term of this patent is extended or adjusted under 35 U.S.C. 154(b) by 352 days.

(21) Appl. No.: 17/601,947

(22) PCT Filed: Apr. 17, 2020

(86) PCT No.: PCT/EP2020/060820
§ 371 (c)(1),
(2) Date: Oct. 7, 2021

(87) PCT Pub. No.: WO2020/212554
PCT Pub. Date: Oct. 22, 2020

(65) Prior Publication Data
US 2022/0133248 A1    May 5, 2022

(30) Foreign Application Priority Data
Apr. 17, 2019    (EP) .................................... 19169880

(51) Int. Cl.
*A61B 6/51*    (2024.01)
*A61B 6/03*    (2006.01)
(Continued)

(52) U.S. Cl.
CPC ................ *A61B 6/51* (2024.01); *A61B 6/032* (2013.01); *A61B 6/462* (2013.01); *G02B 27/017* (2013.01);
(Continued)

(58) Field of Classification Search
CPC ........... A61B 6/032; A61B 6/14; A61B 6/466; A61B 6/5247; A61B 6/463; A61B 6/462;
(Continued)

(56) References Cited

U.S. PATENT DOCUMENTS

2017/0325909 A1* 11/2017 Gao ........................ A61B 6/032
2018/0168781 A1*  6/2018 Kopelman ............. A61B 90/36
2018/0184998 A1*  7/2018 Nyholm .................... A61B 6/12

FOREIGN PATENT DOCUMENTS

JP    2007136133 A    6/2007
JP    2009529951 A    8/2009
(Continued)

OTHER PUBLICATIONS

International Search Report; PCT/EP2020/060820; Jul. 24, 2020 (completed); Aug. 6, 2020 (mailed).
(Continued)

*Primary Examiner* — Irakli Kiknadze
(74) *Attorney, Agent, or Firm* — DENTSPLY SIRONA INC.

(57) ABSTRACT

An apparatus for real-time visualizing a movement of a lower jaw versus an upper jaw including: an input interface for receiving a two-dimensional image signal of the craniomaxillofacial area of the patient from a camera and a three-dimensional jaw model of the craniomaxillofacial area of the patient being precalculated based on volume data; a registration unit for registering the three-dimensional jaw model with the two-dimensional image signal in a first jaw position of the lower jaw versus the upper jaw and in a
(Continued)

second jaw position of the lower jaw versus the upper jaw; an imaging unit for generating a two-dimensional depth-view of the craniomaxillofacial area from the three-dimensional jaw model based on the conducted registrations and the two-dimensional image signal, the two-dimensional depth-view including a structure underlying an image area of the two-dimensional image signal; and an output interface for outputting the two-dimensional depth-view.

15 Claims, 4 Drawing Sheets

(51) Int. Cl.
*A61B 6/46* (2024.01)
*G02B 27/01* (2006.01)
*G06F 3/01* (2006.01)

(52) U.S. Cl.
CPC ...... *G06F 3/011* (2013.01); *G02B 2027/0138* (2013.01); *G02B 2027/014* (2013.01); *G02B 2027/0178* (2013.01)

(58) Field of Classification Search
CPC ... A61B 6/5294; A61B 5/0035; A61B 5/1114; A61B 5/1127; A61B 6/12; A61B 6/4417; A61B 6/501; A61B 5/0077; A61B 5/4542; A61B 6/461; A61B 6/00; A61B 6/03; A61B 6/5223; A61B 5/055; A61B 6/51; G02B 27/017; G02B 2027/0138; G02B 2027/014; G02B 2027/0178; G06T 19/006; G06T 2210/41; G06T 19/20; G06T 7/33; G06T 2219/2004; G06F 3/011; A61C 19/045; A61C 9/004
USPC .......................................................... 378/38
See application file for complete search history.

(56) References Cited

FOREIGN PATENT DOCUMENTS

| | | |
|---|---|---|
| JP | 2017200537 A | 11/2017 |
| JP | 2018126251 A | 8/2018 |
| WO | 2015123759 A1 | 8/2015 |

OTHER PUBLICATIONS

International Preliminary Report on Patentability; PCT/EP2020/060820; Jul. 24, 2020 (completed); Aug. 6, 2020 (mailed).
Written Opinion of the International Searching Authority; PCT/EP2020/060820; Jul. 24, 2020 (completed); Aug. 6, 2020 (mailed).
Japanese Office Action dated Feb. 6, 2024.

* cited by examiner

APPARATUS FOR REAL-TIME VISUALIZING A MOVEMENT OF A LOWER JAW VERSUS AN UPPER JAW IN A CRANIOMAXILLOFACIAL AREA OF A PATIENT IN DENTAL DIAGNOSTICS

CROSS-REFERENCE TO RELATED APPLICATIONS

This is a National Phase application of International Application No. PCT/EP2020/060820, filed Apr. 17, 2020, which claims the benefit of and priority to European Application Ser. No. 19169880.2 filed on Apr. 17, 2019, which are herein incorporated by reference for all purposes.

BACKGROUND OF THE INVENTION

The present invention relates to an apparatus for real-time visualizing a movement of a lower jaw versus an upper jaw in a craniomaxillofacial area of a patient in dental diagnostics. The present invention further relates to a system and a method for visualizing a movement of a lower jaw versus an upper jaw in a craniomaxillofacial area of a patient in dental diagnostics.

Temporomandibular joint dysfunction (TMD) refers to a symptom complex resulting from a dysfunction of the muscles of mastication and the temporomandibular joints connecting the mandible to the skull. TMD is a wide-spread condition and can lead to pain and restricted mandibular movement. Further symptoms include headache, migraine, neck pain, back pain and tinnitus. Reasons include stress, teeth malpositioning or missing teeth etc. The symptoms can become chronic and detrimental to quality of life. One option for treating TMD and other related conditions is to make use of an occlusal splint corresponding to mouth guard for covering the teeth and/or gum. Usually, such splints are worn during sleep to prevent damage to the teeth and to treat possible defective jaw positions.

In order to diagnose TMD and to manufacture a suitable occlusal splint, dental function diagnostics is used to determine the individual mandibular movement of a patient. To match the anatomical data with the movement data of the jaw, current dental diagnostics approaches in this area require different time-consuming steps. In addition, current approaches are limited to special predetermined courses of movement, which have to be tracked with specialized equipment. In particular, an X-ray tomography scan is conducted in a first step, movement data of the patient's jaw is recorded in a second step, an optical image of the patient and a fusion of the data is conducted in a last step. It then becomes possible to visualize the movement on a computer display for diagnosis and therapy planning.

However, apart from being costly and time-consuming, this approach can also lead to inaccuracies due to the limited flexibility with respect to patient-individual movement. This becomes even more critical since it is usually not possible to obtain direct patient feedback due to the separation of the steps of recording and visualizing.

In view of the above, the present invention faces the challenge of improving dental diagnostics with respect to conditions relating to mandibular movement. In particular, the present invention aims at providing a tool for medical personnel for diagnosing conditions relating to mandibular movement.

SUMMARY OF THE INVENTION

To solve this problem, a first aspect of the present invention relates to an apparatus for real-time visualizing a movement of a lower jaw versus an upper jaw in a craniomaxillofacial area of a patient in dental diagnostics, comprising:

an input interface for receiving a two-dimensional image signal of the craniomaxillofacial area of the patient from a camera and a three-dimensional jaw model of the craniomaxillofacial area of the patient being pre-calculated based on volume data;

a registration unit for registering the three-dimensional jaw model with the two-dimensional image signal in a first jaw position of the lower jaw versus the upper jaw and in a second jaw position of the lower jaw versus the upper jaw;

an imaging unit for generating a two-dimensional depth-view of the craniomaxillofacial area from the three-dimensional jaw model based on the conducted registrations and the two-dimensional image signal, said two-dimensional depth-view including a structure underlying an image area of the two-dimensional image signal; and an output interface for outputting the two-dimensional depth-view.

In another aspect, the present invention relates to a system for visualizing a movement of a lower jaw versus an upper jaw in a craniomaxillofacial area of a patient in dental diagnostics, comprising:

an apparatus as defined above; and augmented reality glasses having a camera for generating the two-dimensional image signal and a display for displaying the two-dimensional depth-view, wherein the display is preferably semi-transparent.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

The present invention is based on the idea of making use of augmented reality glasses for allowing a real-time visualization of a movement of the jaw of the patient. A camera of augmented reality glasses is used for recording a two-dimensional image signal of the craniomaxillofacial area of the patient. Further, a pre-calculated three-dimensional jaw model of the craniomaxillofacial area of the patient, which is pre-calculated based on a previously conducted X-ray tomography scan, is obtained. A registration of the three-dimensional jaw model with the two-dimensional image signal is carried out in two jaw positions of the lower jaw versus the upper jaw. Based on this, it becomes possible to generate a two-dimensional depth-view of the craniomaxillofacial area of the patient corresponding to a perspective illustration of the anatomical structures underlying the image area of the two-dimensional image signal. In other words, a view of the three-dimensional jaw model corresponding to the view of the camera of the augmented reality glasses and the respective current position of the lower jaw versus the upper jaw is generated. This two-dimensional depth-view can then be displayed on a display of the augmented reality glasses in order to overlay the real world observed by the person wearing the augmented reality glasses with information on the anatomic structures underlying the observed area. The reality is augmented with information on the underlying structures to allow patient interaction and feedback during dental diagnostics. The patient can move his jaw and the movement of the temporomandibular joint is made visible to allow accurate diagnosis and therapy planning.

In comparison to previous approaches in the field of dental function diagnostics, the present invention thus allows a direct diagnosis based on visualized individual mouth movements of a patient. It is not required to make use of optical markers in a separate registration procedure. Costly and time-consuming processing steps of previous approaches can be saved albeit improving the quality of the diagnostics. A dentist or another medical personnel is provided with a tool for directly visualizing the effects of a movement of the jaws on the temporomandibular joint in order to arrive at an accurate diagnosis and determine an optimal treatment plan. It becomes possible to make use of simple prototypes for determining an optimal therapy position of an occlusal splint.

In comparison to previous approaches of making use of augmented reality in medical approaches as, e.g., presented in WO 2015/123759 A1, a registration in two different positions of the lower jaw versus the upper jaw is used for deriving the two-dimensional depth-view. The use of two registrations makes it possible to visualize the movement of the jaw. Thereby, augmented reality can be used in diagnostic applications and not only for visualizing aesthetic effects of dental appliances or dental restorations.

In a preferred embodiment, the registration unit is configured to register the three-dimensional jaw model in a first jaw position with closed bite and in a second jaw position with fully opened bite. The first jaw position is a position in occlusion, the second jaw position is a position in abocclusion at maximal extent. The mouth is shut and opened as much as possible. These registration positions of the jaw make it possible to exploit the full functional range of the temporomandibular joint in the dental function diagnostics. The two-dimensional depth-view can be generated for all different positions of the jaw. An accurate diagnosis of the jaw functions is made possible.

In another preferred embodiment, the registration unit is configured to register the three-dimensional jaw model with the two-dimensional image signal based on an image recognition of a tooth of the patient within the two-dimensional image signal. Additionally or alternatively, a user input can be used. Further additionally or alternatively, a feature extraction of soft tissue contours within the two-dimensional image signal of the patient can be used. The use of a tooth has the advantage that an accurate mapping (registration) becomes possible since the tooth can usually be visually observed by means of the camera and is also represented in the three-dimensional jaw model generated based on volume data. The use of soft tissue contours on the other hand also provides advantages in that it becomes possible to make use of further matching points. Also, soft tissue contours are represented in the three-dimensional jaw model so that these can be exploited to provide an accurate mapping. The use of a user input has the advantage that patient-individual features or features that are relevant for the current diagnosis application can be used. An accurate diagnosis becomes possible.

In an embodiment the imaging unit is configured to generate the two-dimensional depth-view corresponding to a view of the three-dimensional jaw model from an angle of view of the two-dimensional image signal. The two-dimensional depth-view represents a view of the three-dimensional jaw-model from an angle of view equivalent to the angle of view of the two-dimensional image signal. The dentist has a natural view on the underlying structures while the patient moves his jaw.

In a preferred embodiment, the input interface is configured to receive the two-dimensional image signal from the camera of augmented reality glasses. The output interface is configured to output the two-dimensional depth-view on a display of the augmented reality glasses. Preferably, augmented reality glasses are used to allow a dentist to carry out a function diagnosis of a patient. The dentist obtains means for accurately examining a patient and for obtaining real-time information on the effects of movements of the jaw on the temporomandibular joint.

In another preferred embodiment, the output interface is configured to semi-transparently output the two-dimensional depth-view. Additionally or alternatively, the output interface is configured to output the two-dimensional depth-view only in an area of the temporomandibular joints of the patient. If the two-dimensional depth-view is only displayed in an area of the temporomandibular joints, distraction of the dentist is avoided in order to allow accurate diagnosis.

It is possible to make use of a semi-transparent output in case both the two-dimensional image signal and the two-dimensional depth-view are displayed on a screen. For instance, in case virtual reality glasses are used, a semi-transparent output of the two-dimensional depth-view allows carrying out a function diagnosis.

In a preferred embodiment, the apparatus includes an angle unit for determining an angle of view of the camera in relation to the three-dimensional jaw model. The registration unit is configured to register the three-dimensional jaw model with the two-dimensional image signal based on the determined angle of view. If additional information on the angle of view is present, the generation of the two-dimensional depth-view and the mapping of the two-dimensional image signal with the three-dimensional jaw model becomes more accurate and potentially less computationally expensive. Improved mapping quality and/or faster processing can be obtained.

Preferably, the input interface is configured to receive orientation data with information on an orientation of the camera in an external coordinate system. The angle unit is configured to determine the angle of view based on the orientation data. If the orientation of the camera is provided in an external coordinate system, a calculation of the angle of view can be carried out in this external coordinate system. Then, an accurate mapping to the three-dimensional model becomes possible.

In another preferred embodiment, the input interface is configured to receive a user input with information on a desired view. The imaging unit is configured to generate the two-dimensional depth-view based on the user input. In order to further individualize the diagnosis, it is advantageous to make use of user input with information on a desired view of the user. For instance, a dentist can choose to view certain information in a first step and other information in a second step in order to obtain a clearer overview of the situation. Also, certain relevant areas may be selected. Accuracy of the diagnosis can be further improved.

In another preferred embodiment, the input interface is configured to receive the three-dimensional jaw model via a wireless communication connection. In particular, if the apparatus is integrated in augmented reality glasses, the handling is facilitated if no cable connection is required. In addition, the use of a wireless communication connection makes it possible to carry out some processing steps on an external processor that might provide a higher processing power.

In a preferred embodiment of the system of the present invention, the augmented reality glasses include an orientation sensor for determining an angle of view of the camera. It is particularly possible to make use of an inertial measurement unit or an inertial measurement sensor to determine the current angle of view of the augmented reality glasses. This orientation sensor then provides orientation data that can be used to determine the angle of view and to register the three-dimensional jaw model with the two-dimensional image signal.

In another preferred embodiment of the system, the apparatus is integrated into the augmented reality glasses. An integrated system can minimize the required efforts for setup and situation-specific adaption to allow an efficient application.

Herein the lower jaw can particularly correspond to a mandible of a patient. A craniomaxillofacial area particularly includes the area of the teeth, the upper and lower jaw and the temporomandibular joint of a patient. The two-dimensional depth-view of the craniomaxillofacial area is generated in real time for allowing a live visualization. The movement of the lower jaw versus the upper jaw is visualized in real time. For the registration, different standard registration approaches from the fields of image processing can be used. Volume data are particularly data obtained via a medical imaging device. For instance, volume data can be data from an X-ray scanner, a (cone beam) computed tomography (CT) device or a magnetic resonance imaging (MRI) device. Preferably, volume data correspond to X-ray data. It is also possible to make use of combined data from different imaging modalities. With respect to the camera, the two-dimensional image signal and the two-dimensional depth-view, the singular form is used in this application. It is to be understood that more than one camera and/or more than one image signal can be used and that the generated two-dimensional depth view includes multiple separate two-dimensional images, for instance one for each eye of a person.

BRIEF DESCRIPTIONS OF THE DRAWINGS

These and other aspects of the invention will be apparent from and elucidated with reference to the embodiments described hereinafter. In the following drawings FIG. 1 shows a schematic illustration of a system for visualizing a movement of a lower jaw versus an upper jaw according to the present invention;

DETAILED DESCRIPTION OF THE INVENTION

Figure 1:
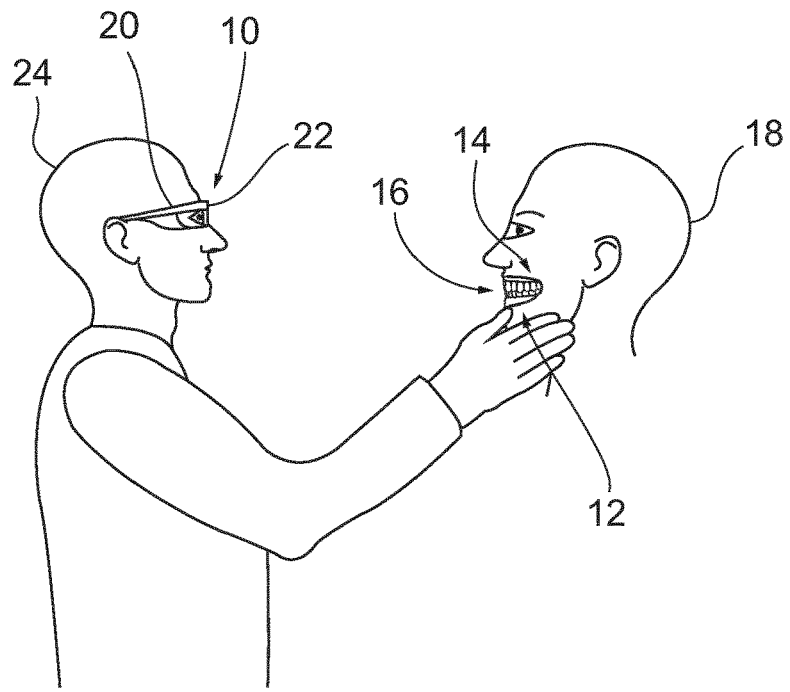

In FIG. 1, a system 10 for real-time visualizing a movement of a lower jaw 12 versus an upper jaw 14 in a craniomaxillofacial area 16 of a patient 18 in dental diagnostics is schematically illustrated. The system 10 includes an apparatus 20 as well as augmented reality glasses 22. In the illustrated embodiment, the apparatus 20 is integrated with the augmented reality glasses 22. The system 10 is applicable in dental diagnostics. In particular, it is possible that a dentist 24 or another caregiver makes use of the system 10 for diagnosing a temporomandibular dysfunction of the patient 18 and for determining an optimal treatment plan for the individual characteristic of the patient 18.

Figure 2:
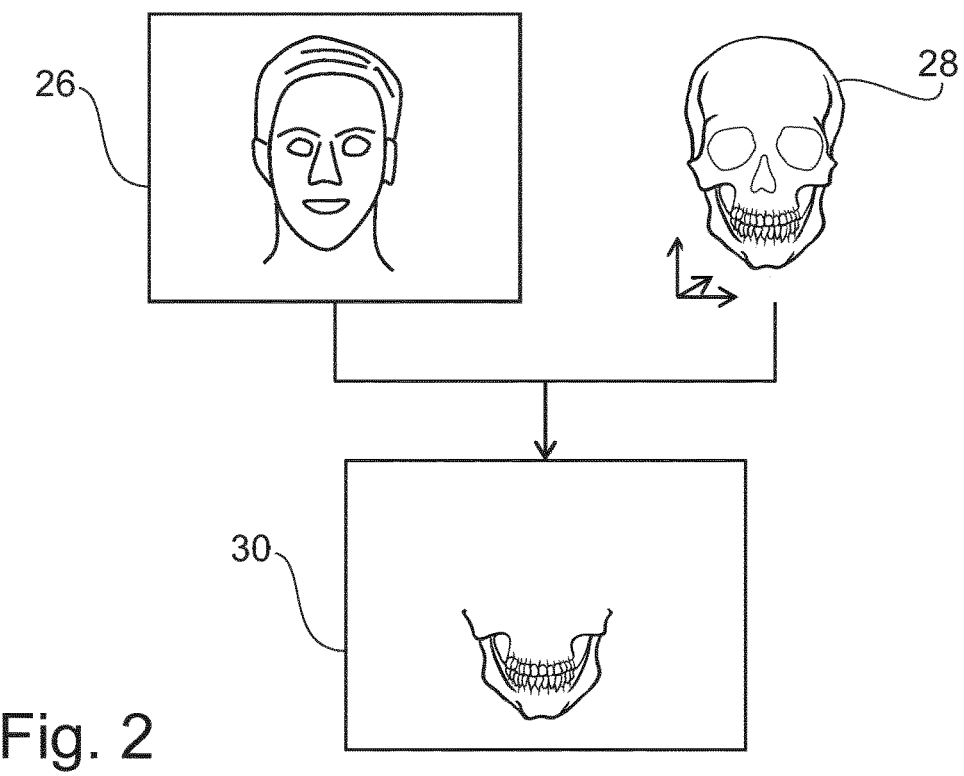
FIG. 2 shows an illustration of the information processing of the present invention.

FIG. 2 schematically illustrates the proposed data processing approach. A two-dimensional image signal 26 of the craniomaxillofacial area of the patient is obtained from a camera. This two-dimensional image signal 26 may particularly correspond to an image of the patient's head. Preferably, the camera of the augmented reality glasses is used for obtaining the two-dimensional image signal 26. In addition, a three-dimensional jaw model 28 is used. This three-dimensional jaw model 28 is precalculated based on volume data. In particular, the three-dimensional jaw model 28 can correspond to a tomography scan of the patient's craniomaxillofacial area. This three-dimensional jaw model 28 includes information on the density of structures in the patient's craniomaxillofacial area. In particular, bones and teeth but also contours of soft tissue are included in the three-dimensional jaw model 28.

The present invention proposes to generate a two-dimensional depth-view 30 of the craniomaxillofacial area based on the real-time two-dimensional image signal 26 and the three-dimensional jaw model 28. This two-dimensional depth-view 30 represents a view of the three-dimensional jaw model 28 from an angle of view that is equivalent to the current angle of view of the two-dimensional image signal. The three-dimensional jaw model 28 is processed to obtain a view from an angle of view similar to the angle of view of the two-dimensional image signal. The current position of the patient's jaw as viewed in the two-dimensional image signal is reflected in the two-dimensional depth-view 30.

This generated two-dimensional depth-view can then be overlaid over the observed real-time image. Thereby, an augmented reality view of the patient's mandibular movement can be realized. The two-dimensional depth-view 30 preferably is a sort of overlay for the two-dimensional image signal 26 to be displayed on a screen of the augmented reality glasses. A dentist or another caregiver can then see the patient through the augmented reality glasses and obtain an overlay image augmenting his observation with the structures underlying the currently viewed area. During the diagnosis it is possible that the dentist communicates with the patient and directs the movements of the patient's jaw. This makes it possible to accurately diagnose the individual jaw movement and determine an optimal position of an occlusal splint.

Figure 3:
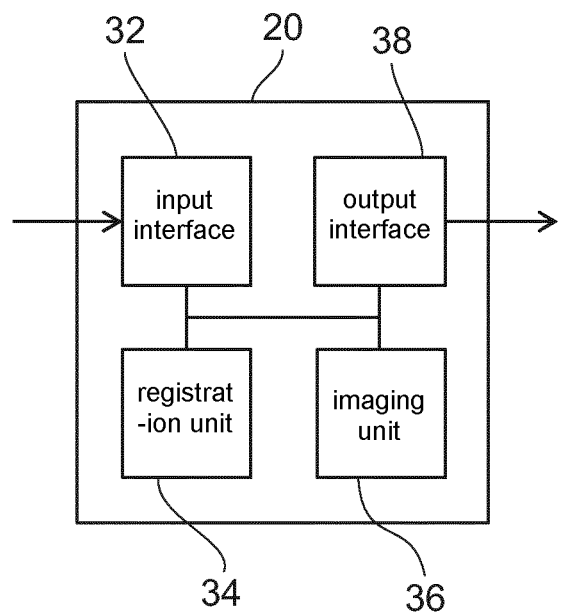
FIG. 3 shows a schematic illustration of an apparatus according to the present invention.

In FIG. 3, the apparatus 20 of the present invention is schematically illustrated. The apparatus includes an input interface 32, a registration unit 34, an imaging unit 36 and an output interface 38. The different interfaces and units may partly or completely be implemented in hard- and/or software. It is possible that the different units and interfaces are integrated in a single unit or implemented in separate units. In particular, the different interfaces and units can be implemented in the form of a processor.

Via the input interface 32, the two-dimensional image signal of the craniomaxillofacial area of the patient is received from a camera. The two-dimensional image signal preferably corresponds to an output signal of a camera. Further, the three-dimensional jaw model is received, e.g.

from a database including the precalculated model. It is possible that this three-dimensional jaw model is pre-calculated based on volume data of the patient obtained in a scan (preferably an X-ray tomography scan) carried out prior to the diagnosis. For this, the input interface may be configured for wireless communication with an external database storing the three-dimensional jaw model.

The registration unit 34 performs an image registration procedure. A first registration is performed when the lower jaw is in a first jaw position versus the upper jaw and another registration is performed when the lower jaw is in a second jaw position versus the upper jaw. Based on the two jaw positions, the features of the two-dimensional image signal are mapped in real time to the features in the three-dimensional jaw model. The two representations of the patient's craniomaxillofacial area are mapped to one another. The image registration thereby includes a mapping or matching of the coordinate systems of the two representations. According to the present invention, the registration unit 34 performs two separate image registration procedures, in which the two-dimensional image signal and the three-dimensional jaw model are transformed into one coordinate system.

For the image registration, different algorithms can be used. For instance, it is possible to make use of intensity-based or feature-based registration algorithms. The basis for the registration may be an image recognition of a tooth of the patient. Ideally, a tooth can be visually observed and recognized in the two-dimensional image signal and is also represented in the three-dimensional jaw model. The characteristic form of a tooth can be identified in both the two-dimensional image signal and the three-dimensional jaw model. A tooth forms a suitable target for registering the three-dimensional jaw model with the two-dimensional image signal.

In the imaging unit 36, the two registrations are used to generate the two-dimensional depth-view of the craniomaxillofacial area. This two-dimensional depth-view corresponds to a real-time visualization of the features included in the three-dimensional jaw model for the area of the two-dimensional image signal and from an equivalent angle of view on the three-dimensional jaw model. In other words, a real-time representation of the underlying bones and teeth etc. for the currently viewed craniomaxillofacial area of the patient is calculated. For this, the imaging unit 36 may be configured to algorithmically determine the intermediate steps between the two registrations. In particular, it is possible to interpolate between the two registrations. In this process standard image processing and movement calculation approaches can be used.

The output interface 38 is configured for outputting the two-dimensional depth-view. Preferably, the outputting is performed in real time. The output interface 38 may be connected to a head-up display of the augmented reality glasses. Thereby, it is possible that a semi-transparent output is performed to overlay the two-dimensional depth-view on the observed portion of the craniomaxillofacial area of the patient. It is possible that the two-dimensional depth-view is only output in an area of the temporomandibular joints of the patient to allow the dentist to obtain information on the dysfunction.

Figure 4:
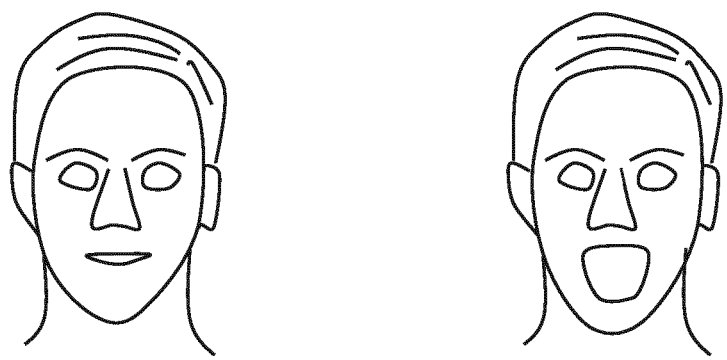
FIG. 4 shows a schematic illustration of a first jaw position and a second jaw position.

In FIG. 4, two preferable jaw positions in which the registrations are performed are illustrated. The first jaw position is illustrated on the left and the second jaw position is illustrated on the right. The first jaw position corresponds to a position with closed bite (occlusion), whereas the second jaw position corresponds to a position with fully opened bite (full abocclusion). In the first jaw position, the teeth of the upper jaw of the patient are in contact with the teeth of the lower jaw of the patient. In the second jaw position, the full functional range of the patient's temporomandibular joints is exploited. The patient opens his mouth as wide as possible.

Figure 5:
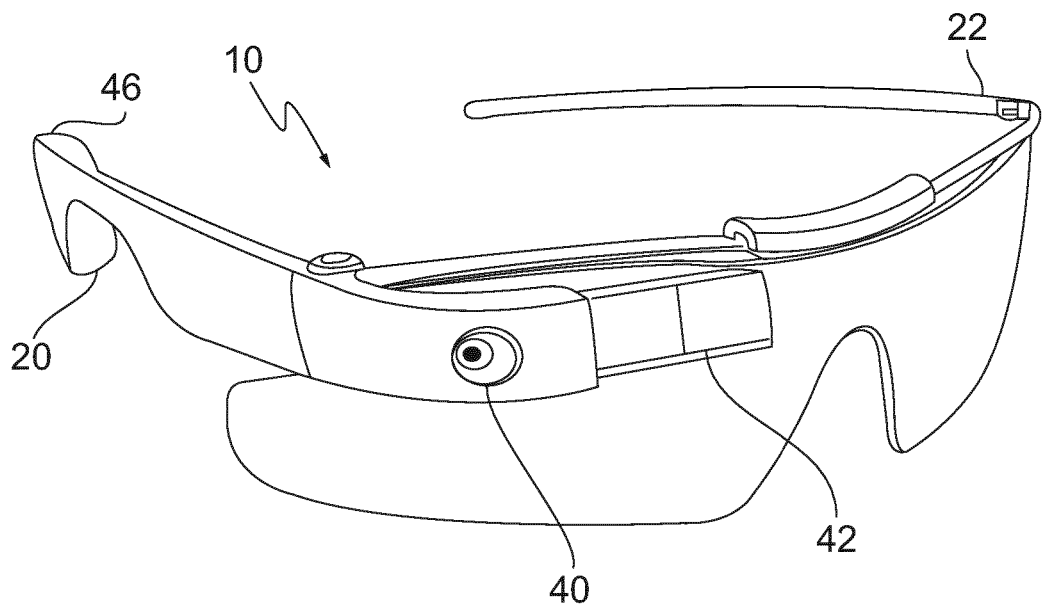
FIG. 5 shows a schematic illustration of a system of the present invention that is integrated into augmented reality glasses.

In FIG. 5, an embodiment of the system 10 of the present invention is illustrated. The system 10 includes augmented reality glasses 22 having a camera 40 as well as a display 42 for displaying the two-dimensional depth-view. The system 10 further includes the apparatus 20 of the present invention. In particular, the apparatus 20 may be implemented in the form of a processor including a wireless communication interface for communicating with further external equipment.

The camera 40 is used for displaying the two-dimensional depth-view. The display 42 is a head-up display that is at least semi-transparent for visual light in order to allow the person wearing the augmented reality glasses 22 to view the reality and, at the same time, view the additional information displayed on the display 42. The camera 40 is connected to the augmented reality glasses so that the angle of view of the glasses corresponds to the angle of view of the camera 40.

In the illustrated embodiment, the system 10 further includes an orientation sensor 46, which preferably includes an internal sensor for determining an orientation of the glasses in an external coordinate system.

Figure 6:
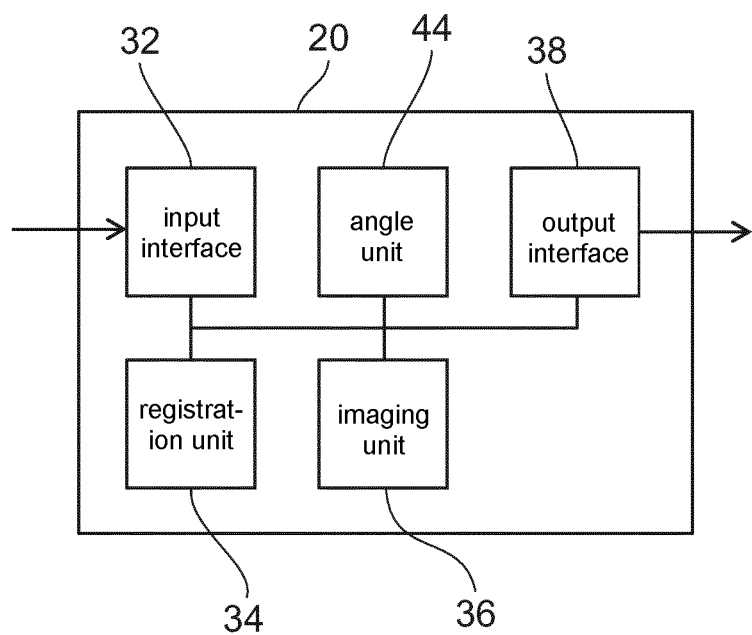
FIG. 6 shows a schematic illustration of another embodiment of an apparatus of the present invention.

In FIG. 6, another embodiment of the apparatus 20 of the present invention is schematically illustrated. In addition to the input interface 32, the registration unit 34, the imaging unit 36 and the output interface 38, the apparatus 20 further includes an angle unit 44 that is configured to determine an angle of view of the camera in relation to the three-dimensional jaw model. This angle unit may also be integrated in a common processing unit.

In an embodiment, it is possible that the two-dimensional depth-view is generated based on user input received via the input interface. Thereby, the two-dimensional depth view can be individualized based on current needs of the dentist. For instance, a dentist may choose to only overlay a certain area and may specify this area via user input. The user input may, e.g., be obtained via a wireless signal from an interface device like a table or the like.

Figure 7:
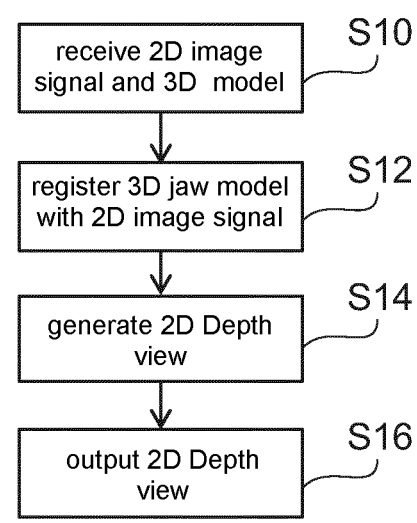
FIG. 7 shows a schematic illustration of a method according to the present invention.

In FIG. 7, an embodiment of a method of the present invention is schematically illustrated. The method includes steps of receiving S10 a two-dimensional image signal and a three-dimensional jaw model, registering S12 the three-dimensional jaw model with the two-dimensional image signal, generating S14 a two-dimensional depth-view and outputting S16 the two-dimensional depth-view. The method of the present invention may particularly be implemented in the form of a software running on a processor of augmented reality glasses. It is, however, also possible that parts of the steps are carried out on an external data processor. For instance, it is possible that the computationally expensive registration is carried out on an external processor having a higher processing power.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the description is intended to be illustrative, but not limiting the scope of the disclosure, as well as other claims. The disclosure, including any readily discernible variants of the teachings herein, defines, in part, the scope of the foregoing claim terminology such that no inventive subject matter is dedicated to the public.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure. Further, such software may also be distributed in other forms, such as via the Internet or other wired or wireless telecommunication systems. A method according to the present invention may particularly be carried out to control the operation of a software-defined radio.

The elements of the disclosed devices, circuitry and system may be implemented by corresponding hardware and/or software elements, for instance appropriated circuits. A circuit is a structural assemblage of electronic components including conventional circuit elements, integrated circuits including application-specific integrated circuits, standard integrated circuits, application-specific standard products, and field-programmable gate arrays. Further a circuit includes central processing units, graphics processing units, and microprocessors which are programmed or configured according to software code. A circuit does not include pure software, although a circuit includes the above described hardware executing software.

The invention claimed is:

1. Apparatus for real-time visualizing a movement of a lower jaw versus an upper jaw in a craniomaxillofacial area of a patient in dental diagnostics, comprising:
   an input interface for receiving a two-dimensional image signal of the craniomaxillofacial area of the patient from a camera and a three-dimensional jaw model of the craniomaxillofacial area of the patient being precalculated based on volume data;
   a registration unit for registering the three-dimensional jaw model with the two-dimensional image signal in a first jaw position of the lower jaw versus the upper jaw and in a second jaw position of the lower jaw versus the upper jaw;
   an imaging unit for generating a two-dimensional depth-view of the craniomaxillofacial area from the three-dimensional jaw model based on the conducted registrations and the two-dimensional image signal, said two-dimensional depth-view including a structure underlying an image area of the two-dimensional image signal; and
   an output interface for outputting the two-dimensional depth-view.

2. Apparatus according to claim 1, wherein the registration unit is configured to register the three-dimensional jaw model in a first jaw position with closed bite and in a second jaw position with fully opened bite.

3. Apparatus according to claim 1, wherein the registration unit is configured to register the three-dimensional jaw model with the two-dimensional image signal based on an image recognition of a tooth of the patient within the two-dimensional image signal; a user input; and/or a feature extraction of soft tissue contours within the two-dimensional image signal of the patient.

4. Apparatus according to claim 1, wherein the imaging unit is configured to generate the two-dimensional depth-view corresponding to a view of the three-dimensional jaw model from an angle of view of the two-dimensional image signal.

5. Apparatus according to claim 1, wherein the input interface is configured to receive the two-dimensional image signal from the camera of augmented reality glasses; and the output interface is configured to output the two-dimensional depth-view on a display of the augmented reality glasses.

6. Apparatus according to claim 1, wherein the output interface is configured to semi-transparently output the two-dimensional depth-view; and/or output the two-dimensional depth-view only in an area of the temporomandibular joints of the patient.

7. Apparatus according to claim 1, with an angle unit for determining an angle of view of the camera in relation to the three-dimensional jaw model, wherein the registration unit is configured to register the three-dimensional jaw model with the two-dimensional image signal based on the determined angle of view.

8. Apparatus according to claim 7, wherein the input interface is configured to receive orientation data with information on an orientation of the camera in an external coordinate system; and the angle unit is configured to determine the angle of view based on the orientation data.

9. Apparatus according to claim 1, wherein the input interface is configured to receive a user input with information on a desired view; and the imaging unit is configured to generate the two-dimensional depth-view based on the user input.

10. Apparatus according to claim 1, wherein the input interface is configured to receive the three-dimensional jaw model via a wireless communication connection.

11. System for visualizing a movement of a lower jaw versus an upper jaw in a craniomaxillofacial area of a patient in dental diagnostics, comprising:
   an apparatus according to claim 1; and
   augmented reality glasses having a camera for generating the two-dimensional image signal and a display for displaying the two-dimensional depth-view, wherein the display is preferably semi-transparent.

12. System according to claim 11, wherein the augmented reality glasses include an orientation sensor for determining an angle of view of the camera.

13. System according to claim 12, wherein the apparatus is integrated into the augmented reality glasses.

14. Method for real-time visualizing a movement of a lower jaw versus an upper jaw in a craniomaxillofacial area of a patient in dental diagnostics, comprising:
   receiving a two-dimensional image signal of the craniomaxillofacial area of the patient from a camera and a three-dimensional jaw model of the craniomaxillofacial area of the patient being precalculated based on volume data;
   registering the three-dimensional jaw model with the two-dimensional image signal in a first jaw position of the lower jaw versus the upper jaw and in a second jaw position of the lower jaw versus the upper jaw;
   generating a two-dimensional depth-view of the craniomaxillofacial area from the three-dimensional jaw model based on the conducted registrations and the two-dimensional image signal, said two-dimensional depth-view including a structure underlying an image area of the two-dimensional image signal; and outputting the two-dimensional depth-view.

15. A non-transitory computer readable storage medium storing a program which, when executed by a computer system, causes the computer system to perform the method of claim 14.

* * * * *